United States Patent [19]

Takács et al.

[11] 4,373,104
[45] Feb. 8, 1983

[54] SULFUR-CONTAINING ISOQUINOLINE DERIVATIVES, PROCESS FOR THE PREPARATION THEREOF AND PHARMACEUTICAL COMPOSITIONS CONTAINING THEM

[75] Inventors: Kálmán Takács; Mária H. Papp; Gabor Kovács; Ilona K. Ajzert; Antal Simay; Péter L. Nagy; Marian E. Puskás; Gyula Sebestyén; István Stadler; Zoltán Sümeghy, all of Budapest, Hungary

[73] Assignee: Chinoin Gyogyszer es Vegyeszeti Termekek Gyara, Budapest, Hungary

[21] Appl. No.: 164,939

[22] Filed: Jul. 1, 1980

[30] Foreign Application Priority Data

Feb. 7, 1979 [HU] Hungary .............................. CI 1944

[51] Int. Cl.³ .................... C07D 217/14; A61K 31/47
[52] U.S. Cl. .................................... 546/145; 424/258; 544/32; 260/244.4; 546/146; 546/147; 546/148; 546/149
[58] Field of Search ............... 546/145, 146, 147, 148, 546/149

[56] References Cited

U.S. PATENT DOCUMENTS

| | | | |
|---|---|---|---|
| 3,378,561 | 4/1968 | Montzka | 546/148 |
| 3,389,140 | 6/1968 | Montzka | 546/148 |
| 3,389,141 | 6/1968 | Montzka | 546/148 |
| 3,437,662 | 4/1969 | Gildersleve et al. | 546/145 |

FOREIGN PATENT DOCUMENTS

| | | |
|---|---|---|
| 51-32569 | 7/1976 | Japan . |
| 51-80867 | 7/1976 | Japan . |
| 51-86477 | 7/1976 | Japan . |
| 51-86478 | 7/1976 | Japan . |

*Primary Examiner*—Donald G. Daus
*Assistant Examiner*—James H. Turnipseed
*Attorney, Agent, or Firm*—Karl F. Ross

[57] ABSTRACT

Isoquinolines are disclosed of the formula (I)

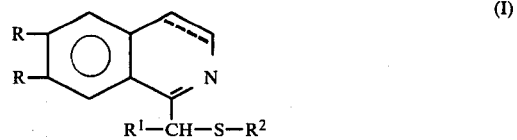

wherein
R independently represents hydrogen, hydroxyl or alkoxy having 1 to 4 carbon atoms,
$R^1$ is hydrogen, alkyl having 1 to 4 carbon atoms and optionally substituted with phenyl, phenyl optionally substituted with one or more halogen or alkoxy group, cyano or carbomoyl,
$R^2$ is phenyl optionally substituted with one or more halogen, alkoxy or carboxyl, or a group of the general formula A

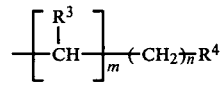

wherein
$R^3$ is hydrogen, a straight or branched chained alkyl having 1 to 4 carbon atoms or phenyl,
m and n independently represent 0, 1 or 2, with the proviso that m+n is at least 1,
$R^4$ is hydrogen, phenyl, hydroxyl, acyloxy, carboxyl, alkoxycarbonyl having 1 to 6 carbon atoms, carbamoyl, carbazoyl or dialkylamino containing 1 to 6 carbon atoms in the alkyl moiety, or
$R^2$ is a straight or branched chained alkylene group having 1 to 6 carbon atoms, and
the dotted line stands for a further carbon-carbon bond or hydrogen atoms in the 3- and 4-positions of the ring, or salts thereof. The new compounds are potent diuretic agents.

28 Claims, No Drawings

SULFUR-CONTAINING ISOQUINOLINE DERIVATIVES, PROCESS FOR THE PREPARATION THEREOF AND PHARMACEUTICAL COMPOSITIONS CONTAINING THEM

This invention relates to new sulfur-containing isoquinoline derivatives and salts and cyclic acid amides thereof. More particularly, the invention concerns new sulfur-containing isoquinoline derivatives of the formula (I)

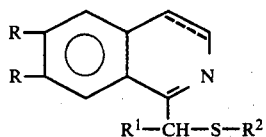

wherein
- R is hydrogen, hydroxyl or alkoxy having 1 to 4 carbon atoms,
- $R^1$ is hydrogen, alkyl having 1 to 4 carbon atoms unsubstituted or substituted with phenyl, phenyl which can be substituted with one or more halogen or alkoxy group, cyano or carbamoyl,
- $R^2$ is phenyl which can be substituted with one or more halogen, alkoxy or carboxyl, or a group of the formula (A)

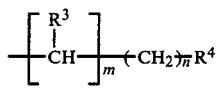

wherein
- $R^3$ is hydrogen, a straight or branched chain alkyl having 1 to 4 carbon atoms or phenyl,
- m and n independently are each 0, 1 or 2 but m+n is at least 1,
- $R^4$ is hydrogen, phenyl, hydroxyl, acyloxy, carboxyl, alkoxycarbonyl having 1 to 6 carbon atoms, carbamoyl, carbazoyl or dialkylamino containing 1 to 6 carbon atoms in the respective alkyl moiety, or
- $R^2$ is straight or branched chain alkylene having 1 to 6 carbon atoms, and
- the dotted line stands for a further carbon-carbon bond or hydrogen atoms in the 3- and 4-positions of the ring, and salts and cyclic acid amides thereof.

According to a further aspect of the invention there is provided a process for the preparation of these compounds.

According to the present invention there are also provided pharmaceutical compositions containing as active ingredient a compound of the formula (I) in admixture with one or more conventional pharmaceutical carriers.

It is known that isoquinoline derivatives which have an analogous structure but contain a heterocyclic $R^2$ in the formula (I) are potent spasmolytic and vasodilating substances (see Published Japanese Patent Applications Nos. 76,32,569; 76,80,867; 76,86,478 and 76,86,477). These analogous compounds were prepared by reacting 1-halomethylisoquinoline derivatives with heterocyclic compounds containing a sulfhydryl group in a manner known per se.

We have surprisingly found that the new isoquinoline derivatives of the formula (I) have valuable pharmaceutical properties. More particularly, they promote the production of prostaglandine-$E_2$ from arachidonic acid and therefore have diuretic, antiasthmatic, antiinflammatory and hypotensive activity.

According to the invention new isoquinoline derivatives of the formula (I) are prepared by the following methods:

(a) The compounds of the formula (I) in which R is hydrogen or alkoxy having 1 to 4 carbon atoms, $R^1$, $R^2$ and the dotted line are as defined above, are prepared by reacting isoquinoline derivatives of the formula (II)

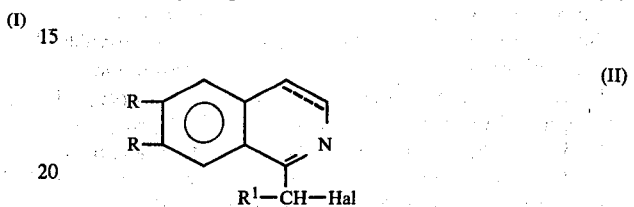

wherein R is as defined immediately hereinabove, $R^1$ and the dotted line are as defined above, and Hal represents halogen, with thiols of the formula (III)

$$R^2-SH \qquad (III)$$

wherein $R^2$ is as defined above.

(b) The compounds of the formula (I) in which R is hydrogen or an alkyl having 1 to 4 carbon atoms, $R^1$ and the dotted line are as defined above, and $R^2$ represents a group of the formula (A), in which $R^3$, $R^4$, m and n are as defined above, are prepared by hydrolyzing isothiuronium salts of the formula (IV)

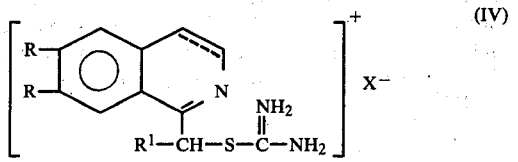

in which
- R is as defined immediately hereinabove, $R^1$ and the dotted line are as defined above, and
- $X^-$ represents one equivalent of an organic or inorganic anion, in an alkaline medium, and subsequently reacting the thiolates of the formula (V)

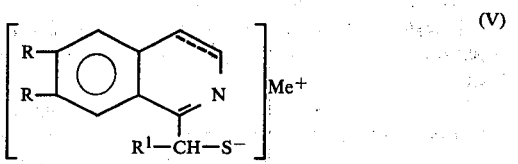

obtained, wherein
- R, $R^1$ and the dotted line are as defined hereinabove and
- $Me^+$ represents one equivalent of an organic or inorganic cation, with halides of the formula (VI)

$$R^2-Hal \qquad (VI)$$

wherein $R^2$ has the same meaning as defined above and Hal stands for a halogen atom.

If desired, the isoquinoline derivatives of the formula (I), wherein $R^1$, $R^2$ and the dotted line are as defined above, and R is alkoxy having 1 to 4 carbon atoms, can be desalkylated into compounds of the formula (I) in which R is a hydroxyl group and $R^1$, $R^2$ and the dotted line are as defined above.

If desired, the compounds of the formula (I), in which $R^2$ represents a group of the formula (A), $R^3$, m and n are as hereinbefore defined and $R^4$ is hydroxyl can be converted into derivatives which contain an acyloxy group in place of $R^4$ by acylation.

The isoquinoline derivatives of the formula (I) in which $R^2$ stands for a group of the formula (A), $R^3$, m and n are as defined above, and $R^4$ is carboxyl or carbalkoxy while R, $R^1$ and the dotted line are as hereinbefore defined, can be converted into other isoquinoline derivatives of the formula (I), in which $R^2$ is a group of the general formula (A), in which R, $R^1$, $R^3$, m, n and the dotted line are as defined above, and $R^4$ is an alkoxycarboxyl group having 1 to 6 carbon atoms, carbamoyl or carbazoyl group, by esterification, amidation and formation of a hydrazide, respectively. The same starting compounds can be converted into cyclic acid amides of the formula (VII)

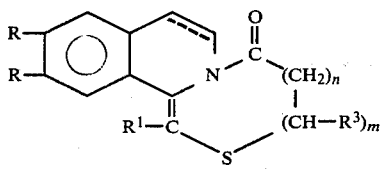

(VII)

wherein R, $R^1$, $R^3$ and the dotted line are as defined above, by using a suitable dehydrating agent.

The isoquinoline derivatives of the formula (I), in which $R^2$ stands for a 2-carboxyphenyl group, and R, $R^1$ and the dotted line are as hereinbefore defined, can be converted into cyclic acid amides of the formula (VIII)

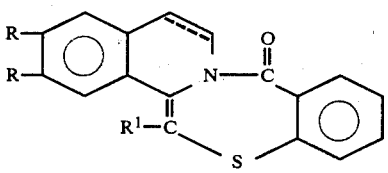

(VIII)

wherein R, $R^1$ and the dotted line are as defined above, by treating with suitable dehydrating agents.

If desired, the compounds of the formula (I) which contain a carboxyl group can be converted into their salts.

The process variant (a) can be accomplished in an organic, preferably in an alcoholic medium, in the presence of acid binding agents. As acid binding agents alkali metal alcoholates, hydroxydes or carbonates can be used. The reaction is carried out at a temperature between 0° C. and 120° C., preferably at the boiling temperature of the solvent employed. In the case of oxidation-sensitive compounds the process is performed under inert atmosphere. As an inert gas nitrogen or argon can advantageously be used. According to a preferred embodiment of the process isoquinoline derivatives of the formula (II) or the solutions thereof are added to a solution of thiols of the formula (III) and the dehydrating agent. A reversed order is, however, also possible.

Isoquinoline derivatives of the formula (II) used as starting materials are either known or can be prepared by literature known methods (DOS No. 2,426,267, J. Chem. Soc., 1931, 36; and Arch. Pharm., 277, 177; 1939).

The alkaline hydrolysis according to process variant (b) is preferably carried out with alkali metal hydroxides, in a mixture of water-miscible organic solvents and water. The reaction is preferably accomplished in aqueous alcohols. It is preferred to promote the progress of hydrolysis by heating the reaction mixture, e.g. by boiling for 1 or 2 hours. The thiolates of the formula (V) produced by hydrolysis need not be separated from the reaction mixture; the halides of the formula (VI) can directly be added into the hydrolysis mixture. To complete the reaction the reaction mixture is preferably boiled also in this reaction step. To avoid oxidation side-reactions the reaction is preferably performed under inert gas atmosphere. The isothiuronium salts of the formula (IV) used as starting compounds are prepared by reacting isoquinoline derivatives of the formula (II) with thiourea.

The conversion of the R alkoxy groups into hydroxy groups is carried out by known desalkylating methods, for example by an acidic reactant, such as pyridine hydrochloride under heating.

The $R^4$ hydroxyl group can be acylated by reactive carboxylic acid derivatives. Such derivatives include for example acid anhydrides and acid halides. The reaction is performed in an inert organic solvent, or in excess of the acylating agent.

The $R^4$ carboxyl group can be esterified by known methods, or can be converted into carbamoyl or carbazoyl groups by reaction with ammonia and hydrazine, respectively. The esters are preferably prepared in an alcoholic medium, by boiling the reaction mixture. The acid amides and acid hydrazides are preferably obtained through the corresponding esters, which are reacted with ammonia or hydrazine.

The cyclic amides of the formula (VII) and (VIII) are preferably prepared by reacting isoquinoline derivatives of the formula (I), in which $R^4$ is carboxyl with dehydrating agents, e.g. acid anhydrides, preferably acetic acid anhydride or dicyclohexyl-carbodiimide. The cyclic amides can be reconverted into the corresponding carboxylic acid by hydrolysis.

The isoquinolyl derivatives of the formula (I), which contain a group capable of forming salts, can be converted into the corresponding salts by reacting with bases and acids, respectively, in a manner known per se.

The isoquinoline derivatives of the formula (I) obtained can be isolated by known techniques, such as filtration, evaporation, crystallization, extraction, and can be purified by typical purification techniques of organic chemistry, for example recrystallization. The preparation of salts can be used also for purification.

The terms "alkyl" or "alkoxy" having 1 to 4 or 1 to 6 carbon atoms refer to straight or branched chain hydrocarbon groups which are attached to the adjacent moiety through an optional carbon atom thereof. These groups include alkyl groups having 1 to 4 carbon atoms, e.g. methyl, ethyl, n-propyl and isopropyl, n-butyl, isobutyl, sec.-butyl and tert.-butyl groups. Alkyl groups having 1 to 6 carbon atoms also include pentyl and hexyl groups. The corresponding alkoxy groups can be derived from the alkyl groups listed above.

The term "halogen" refers to fluorine, chlorine, bromine and iodine atoms.

The term "organic or inorganic bases and acids" is used to refer to hydroxides containing alkali metal, alkaline earth metal, ammonium and various substituted ammonium ions; halohydrogenic acids, inorganic oxyacids, organic aliphatic and aromatic carboxylic acids. The cations and anions, which can be derived therefrom are $Me^+$ cations and $X^-$ anions. Preferred representatives of said bases are sodium, potassium, and calcium hydroxides, ammonium hydroxide; preferred acids are hydrochloric acid, sulfuric acid, phosphoric acid, benzoic acid, oxalic acid, tartaric acid and the cations and anions are preferably derived from the above-listed bases and acids.

The effect of the compounds of the formula (I) on the biosynthesis of prostaglandins was determined by a known technique (J. Biol. Chem., 246, 6700; 1971). As an enzyme source a homogenizate of sheep spermatocele and as a substrate arachidonic acid were used. The transformation of the substrate, which involves oxygen consumption, was monitored on the basis of the change of the concentration of dissolved oxygen, which was measured by a Clark electrode. During the measurements the concentration of the active compounds, which involved a 50% and 100%, respectively, increase in the oxygen consumption were determined. The concentrations were expressed in $\mu M/lit$. The results obtained are contained in the Table below.

TABLE

The effect of the compounds of the formula
(I) on the activity of cyclic oxygenase
Substrate: arachidonic acid

| Example No. | $AC_{50\%}$ | $AC_{100\%}$ |
| --- | --- | --- |
| 3 | 100 | 200 |
| 4 | 70 | 140 |
| 5 | 40 | 80 |
| 6 | 60 | 225 |
| 8 | 48 | 96 |
| 9 | 95 | |
| 12 | 105 | |
| 14 | 280 | 395 |
| 15 | 62 | 124 |
| 18 | 69 | 138 |
| 22 | 720 | 1800 |

The diuretic activity of the compounds of the formula (I) was tested on rats. The quantity of the urine passed in 4 hours and of the discharged $Na^+$ and $K^+$ ions were determined by known methods (Arzneimitt. Forsch. 27, 559; 1978). The antiinflammatory activity was tested in paw oedema on rats. The oedema was induced by carrageenien and the inhibition was expressed in %.

According to a test carried out on isolated trachea of guinea pigs (J. Pharm. Pharmac. 31, 798; 1979) the compounds prepared according to the invention have a relaxant activity. The compound of Example 9 has the same activity as theophylline while the compound of Example 4 shows a five-times higher activity than theophylline related to a 95 to 100% relaxation. A 1 $\mu g/ml$. dose of the product of Example 4 is five-times more effective than theophylline but the compound of Example 9 has only half of its effect. The activity of the compounds obtained in Example 4 is significant also at a dose of 0.1 $\mu g/ml$.

On ileum of guinea pigs the compounds according to the invention show an antagonistic activity against acetylcholine and histamine (Turner, R., Screening Methods in Pharmacology, Academy Press, New York, 1965, p. 42–43). When used in a 50 $\mu g/ml$. antagonistic dose against acetylcholine theophylline results in a 16% inhibition. The compound of Example 9 has the same activity, while the product of Example 4 is six-times more active. The maximum inhibition in the case of theophylline is 30% (at a dose of 200 $\mu g/ml$.), of the compound of Example 4 is 100% (in a dose of 50 $\mu g/ml$.), in the case of the compound obtained in Example 9 is 55% (in a dose of 100 $\mu g/ml$.).

When used in a 50 $\mu g/ml$. antagonistic dose theophylline causes a 18% inhibition against histamine. The compound of Example 9 has the same effect as theophylline. The compound obtained in Example 4 is six-times more potent. The maximum inhibition for theophylline is 37% (in a dose of 200 $\mu g/ml$.), for the product of Example 4 is 100% (50 $\mu g/ml$.) for the compound of Example 9 is 26% (100 $\mu g/ml$.).

The serotonine antagonistic effect of the compounds according to the invention was examined on a gastric fundus strip of rats (Br. J. Pharm. 12, 344–349; 1957). A 10 $\mu g/ml$. antagonistic dose of theophylline produced a 8%, that of the compound of Example 8 a 8%, that of the compound of Example 6 a 16% and that of the compound obtained in Example 4 a 80% inhibition.

Compounds of the formula (I) can be used in therapy in the form of compositions containing the active ingredients along with inert, solid or liquid, organic or inorganic carriers. The compositions are prepared by conventional techniques of pharmaceutical industry.

The compositions can be formulated as formulations suitable for oral, parenteral administration or for inspiration. Suitable formulations include for example tablets, dragees, capsules, lozenges, powder mixtures, aerosol sprays, aqueous suspensions or solutions, injectable solutions or syrups. The formulations can contain suitable solid diluents or carriers, a sterile aqueous solvent or a non-toxic organic solvent. The formulations prepared for oral administration also contain conventional sweetening and aromatizing agents.

As a carrier of tablets for oral administration for example lactose, sodium citrate, calcium carbonate and disintegrating substances for example starch, alginic acid; lubricants, for example talc, sodium-lauryl sulfate, or magnesium stearate can be used.

Typical carriers for capsules are lactose and polyethylene glycol. The aqueous suspensions can also contain emulsifying or suspending agents. In the suspensions prepared with organic diluents for example ethanol, glycerine and chloroform can be used.

The compositions suitable for parenteral administration or inspiration are suitable solutions or suspensions of the active ingredient. Suitable solvents, or diluents are for example peanut oil, sesame oil, polypropylene glycol or water. The injection formulations can be administered intravenously, intramuscularly or subcutaneously. The injection solutions are preferably produced with water and the pH is adjusted to a suitable value. Isotonic salt or glucose solutions can also be prepared.

If the compositions are to be used for curing asthma, they are administered through inspiration by the conventional inhalating and inspirating equipments.

The pharmaceutical compositions can contain 0.005 to 90% of active ingredient. The effective daily dose can be varied within a wide range depending on the state, age, weight of the patient, on the formulation used and on the activity of the specific active ingredient used.

In the case of oral administration the daily dose generally is 0.05 to 15 mg/kg. and if the administration is effected by inspiration or intravenously, the compounds can be administered in a 0.001 to 5 mg/kg. dose one or more times a day. The above data are for orientation only and in concrete cases variation in both directions are allowed.

Capsules containing 40 mg. of active ingredient can for example be prepared as follows:
  400.0 g. of a compound of the formula (I)
  1590.0 g. of lactose and
  10.0 g. of magnesium stearate
are admixed homogenously and filled into hard gelatine capsules in 200.0 mg. portions. 10 000 capsules containing 40 mg. of active ingredient are prepared.

Further details of the invention are to be found in the following Examples which illustrate but do not limit the invention.

EXAMPLE 1

To 8.0 g. of [α-cyano-α-6,7-dimethoxy-3,4-dihydro-1-isoquinolyl]-methyl-isothiuronium bromide 80 ml. of a 96% alcohol and 24 ml. of a 10% aqueous sodium hydroxide solution are added and the reaction mixture is refluxed for two hours. 2 ml. of ethyl iodide in 20 ml. of alcohol are then added and the mixture is refluxed for another six hours. The solvent is evaporated in vacuo and to the residue water is added. 5.6 g. of α-(ethylmercapto)-6,7-dimethoxy-3,4-dihydro-1-isoquinolyl-acetonitrile are obtained, melting at 113° to 115° C. after crystallization from absolute ethanol.

Analysis for $C_{15}H_{18}N_2O_2S$ (290.38): calculated: C, 62.04%; H, 6.25%; N, 9.65%; S, 11.04%. found: C, 62.00%; H, 6.10%; N, 9.73%; S, 11.15%.

EXAMPLE 2

Starting from 8.0 g S-(α-cyano-α-6,7-dimethoxy-3,4-dihydro-isoquinolyl)-methyl-isothiuronium bromide and 2.5 ml. of allyl bromide and following the procedure described in Example 1, 5.1 g. of α-(allylmercapto)-6,7-dimethoxy-3,4-dihydro-isoquinolyl-acetonitrile are obtained, melting at 146° to 147° C. after recrystallization from absolute ethanol.

Analysis for $C_{16}H_{18}N_2O_2S$ (302.35): calculated: C, 63.56%; H, 6.00%; N, 9.27%. found: C, 63.77%; H, 6.25%; N, 9.54%.

EXAMPLE 3

Starting from 8.0 g. of S-(α-cyano-α-6,7-dimethoxy-3,4-dihydro-1-isoquinolyl)-methyl-isothiuronium bromide and 1.7 g. of ethylene chlorohydrine and following the procedure described in Example 1, 6.3 g. of α-(2-hydroxy-ethylmercapto)-6,7-dimethoxy-3,4-dihydro-1-isoquinolyl-acetonitrile are obtained, melting at 138° to 140° C. after recrystallization from a 50% aqueous ethanol solution.

Analysis for $C_{15}H_{18}N_2O_3S$ (306.38): calculated: C, 58.80%; H, 5.92%; N, 9.14%; S, 10.47%. found: C, 59.07%; H, 5.67%; N, 9.08%; S, 10.18%.

DL>500 mg/kg. per os on mice. A 100 mg/kg dose of the compound on rats in paw oedema test resulted in a 20% inhibition.

EXAMPLE 4

Starting from 8.0 g. of S-(α-cyano-α-6,7-dimethoxy-3,4-dihydro-1-isoquinolyl)-methyl-isothiuronium bromide and 2.0 g. of 3-chloropropanol and following the procedure described in Example 1, 6.2 g. of α-(3-hydroxy-propylmercapto)-6,7-dimethoxy-3,4-dihydro-1-isoquinolyl-acetonitrile are obtained, melting at 155° to 156° C. after recrystallization from absolute ethanol.

Analysis for $C_{16}H_{20}N_2O_3S$ (320.41): calculated: C, 59.98%; H, 6.29%; N, 8.74%; S, 10.01%. found: C, 59.96%; H, 6.33%; N, 8.89%; S, 10.39%.

$LD_{50}$>500 mg/kg. p.o. on mice. A 100 mg/kg. p.o. dose of the compound on rats in paw oedema test resulted in a 20% inhibition.

EXAMPLE 5

To 10.0 g. of S-(α-cyano-α-3,4-dihydro-1-isoquinolyl)-methyl-isothiuronium bromide 200 ml. of a 96% alcohol and 40 ml. of a 10% aqueous sodium hydroxide solution are added and the reaction mixture is refluxed for two hours. A solution of 2.9 g. of chloroacetic acid in 30 ml. of alcohol is then added and the mixture is refluxed for another four hours. The solvent is evaporated in vacuo and 25 ml. of water are added to the residue. The solution is decolored by charcoal, filtered and its pH is adjusted to 4 with concentrated hydrochloric acid. 4.9 g. of α-carboxy-methyl-mercapto-3,4-dihydro-isoquinolyl-acetonitrile are obtained, melting at 159°–160° C. after recrystallization from absolute ethanol.

Analysis for $C_{13}H_{12}N_2O_2S$: calculated: C, 59.98%; H, 4.65%; N, 10.76%; S, 12.32%. found: C, 59.77%; H, 4.72%; N, 10.53%; S, 11.94%.

EXAMPLE 6

Following the procedure of Example 5 but starting from 19.2 g. of S-(α-cyano-α-6,7-dimethoxy-3,4-dihydro-1-isoquinolyl)-methyl-isothiuronium bromide and 4.7 g. of chloroacetic acid 13.3 g. of α-carboxymethyl-mercapto-6,7-dimethoxy-3,4-dihydro-1-isoquinolyl-acetonitrile are obtained, melting at 173° to 175° C. after recrystallization from absolute ethanol.

Analysis for $C_{15}H_{16}N_2O_4S$ (320.37): calculated: C, 56.23%; H, 5.03%; N, 8.75%; S, 10.01%. found: C, 65.22%; H, 4.89%; N, 8.87%; S, 10.04%.

$LD_{50}$>500 mg/kg. p.o. on mice. A 2 mg/kg. dose of the compound increased the quantity of the urine secreted to the same extent as a 2 mg/kg. p.o. dose of Hypothiazid.

EXAMPLE 7

Following the procedure described in Example 5 but starting from 2.5 g. of S-(1-isoquinolyl-methyl)-isothiuronium chloride and 0.9 g. of chloroacetic acid 1.3 g. of S-(1-isoquinolyl-methyl)-thioglycolic acid are obtained, melting at 186° to 187° C. after recrystallization from absolute ethanol.

Analysis for $C_{12}H_{11}NO_2S$ (233.29): calculated: C, 61.78%; H, 4.75%; N, 6.01%; S, 13.75%. found: C, 61.96%; H, 4.89%; N, 6.01%; S, 14.10%.

EXAMPLE 8

Following the procedure described in Example 5 but starting from 10.0 g. of S-(α-cyano-α-3,4-dihydro-1-isoquinolyl)-methyl-isothiuronium bromide and 3.4 g. of 3-chloropropionic acid, 5.4 g. of α-(2-carboxyethyl)-mercapto-3,4-dihydro-1-isoquinolyl-acetonitrile are obtained, melting at 149° to 150° C. after recrystallization from absolute ethanol.

Analysis for $C_{14}H_{14}N_2O_2S$ (274.34): calculated: C, 61.29%; H, 5.14%; N, 10.21%; S, 11.69%. found: C, 61.58%; H, 5.30%; N, 10.20%; S, 11.97%.

EXAMPLE 9

Following the procedure described in Example 5 but starting from 8.0 g. of S-($\alpha$-cyano-$\alpha$-6,7-dimethoxy-3,4-dihydro-1-isoquinolyl)-methyl-isothiuronium bromide and 2.3 g. of 3-chloropropionic acid 5.5 g. of $\alpha$-(2-carboxyethyl)-mercapto-6,7-dimethoxy-1-isoquinolyl-acetonitrile are obtained, melting at 169° to 170° C. after recrystallization from absolute ethanol.

Analysis for $C_{16}H_{18}N_2O_4S$ (334.39): calculated: C, 57.47%; H, 5.43%; N, 8.38%; S, 9.59%. found: C, 57.44%; H, 5.49%; N, 8.34%; S, 9.70%.

$LD_{50} > 500$ mg/kg. p.o. on mice. A 2 mg/kg. dose of the compound increased the quantity of the urine secreted to the same extent as a 2 mg/kg. p.o. dose of Hypothiazid.

EXAMPLE 10

Following the procedure described in Example 5 but starting from 10.0 g. of S-($\alpha$-cyano-$\alpha$-6,7-diethoxy-3,4-dihydro-1-isoquinolyl)-methyl-isothiuronium bromide and 2.6 g. of 3-chloropropionic acid, 6.0 g. of $\alpha$-(2-carboxyethyl)-mercapto-6,7-diethoxy-3,4-dihydro-1-isoquinolyl-acetonitrile are obtained, melting at 106° to 108° C. after recrystallization from a 50% of an aqueous alcohol solution.

Analysis for $C_{18}H_{22}N_2O_4S$ (352.45): calculated: S, 8.85%. found: S, 9.04%.

EXAMPLE 11

Following the procedure described in Example 5 but starting from 15.0 g. of S-(1-isoquinolylmethyl)-isothiuronium chloride and 6.4 g. of 3-chloro-propionic acid, 8.0 g. of S-(1-isoquinolyl-methyl)-3-mercapto-propionic acid are obtained, melting at 126° to 130° C. after recrystallization from absolute ethanol.

Analysis for $C_{13}H_{13}NO_2S$ (247.31): calculated: S, 12.97%. found: S, 12.65%.

EXAMPLE 12

Following the procedure described in Example 5 but starting from 8.0 g. of S-($\alpha$-cyano-$\alpha$-6,7-dimethoxy-3,4-dihydro-1-isoquinolyl)-methyl-isothiuronium bromide and 2,3 g. of 2-chloropropionic acid, 5.1. g. of $\alpha$-(1-carboxy-1-ethyl)-mercapto-6,7-dimethoxy-3,4-dihydro-1-isoquinolyl-acetonitrile are obtained, melting at 155° to 158° C. after recrystallization from ethyl acetate.

Analysis for $C_{16}H_{18}N_2O_4S$ (334.39): calculated: S, 9.59%. found: S, 9.22%.

EXAMPLE 13

Following the procedure described in Example 5 but starting from 15.0 g. of S-(1-isoquinolyl-methyl)-isothiuronium chloride and 6.4 g. of 2-chloropropionic acid, 7.1 g. of S-(1-isoquinolyl-methyl)-2-mercapto-propionic acid are obtained, melting at 153° to 156° C. after recrystallization from a 96% ethanol.

Analysis for $C_{13}H_{13}NO_2S$ (247.31): calculated: C, 63.13%; H, 5.30%; N, 5.66%; S, 12.97%. found: C, 63.10%; H, 5.61%; N, 5.33%; S, 12.52%.

EXAMPLE 14

To 8.0 g. of S-($\alpha$-cyano-$\alpha$-6,7-dimethoxy-3,4-dihydro-1-isoquinolyl)-methyl-isothiuronium bromide 80 ml. of a 96% ethanol and 24 ml. of a 10% aqueous sodium hydroxide solution are added and the reaction mixture is refluxed for 20 minutes. Into the boiling solution a solution of 3.6 g. of 2-diethyl-amino-ethyl-chloride hydrochloride in 10 ml. of water is added dropwise. After stirring for further three hours the solvent is evaporated in vacuo, the mixture is decolored with charcoal, filtered and acidified with an alcoholic hydrochloric acid solution. From the solution 6.4 g. of $\alpha$-(2-diethylaminoethyl)-mercapto-6,7-dimethoxy-3,4-dihydro-1-isoquinolyl-acetonitrile hydrochloride are precipitated, melting at 169° to 172° C. after recrystallization from absolute ethanol.

Analysis for $C_{19}H_{28}N_3O_2SCl$ (397.96): calculated: C, 57.34%; H, 7.09%; N, 10.56%; S, 8.06%; Cl, 8.91%. found: C, 57.37%; H, 7.05%; N, 10.09%; S, 7.83%; Cl 9.00%.

EXAMPLE 15

Following the procedure described in Example 14 but starting from 8.0 g. of S-($\alpha$-cyano-$\alpha$-6,7-dimethoxy-3,4-dihydro-1-isoquinolyl)-methyl-isothiuronium bromide and 3.0 g. of 2-dimethylamino-ethyl-chloride hydrochloride, 6.6 g. of $\alpha$-(2-dimethylaminoethyl)-mercapto-6,7-dimethoxy-3,4-dihydro-1-isoquinolyl-acetonitrile hydrochloride are obtained, melting at 210° to 212° C. after recrystallization from absolute alcohol.

Analysis for $C_{17}H_{24}N_3O_2SCl$ (369.91): calculated: N, 11.36%; S, 8.67%; Cl, 9.59%. found: N, 11.21%; S, 8.69%; Cl, 9.78%.

EXAMPLE 16

Into a sodium ethylate solution prepared from 0.46 g. of sodium and 50 ml. of absolute alcohol 1.54 g. of thiosalicylic acid are added. The reaction mixture is brought to boil and into the boiling solution a solution of 3.1 g. of $\alpha$-bromo-1-cyano-methyl-6,7-dimethoxy-3,4-dihydro-isoquinoline in 100 ml. of absolute ethanol is added dropwise. The mixture is boiled for another half an hour, and the solvent is evaporated in vacuo. To the evaporation residue 50 ml. of water and a few drops of a 10% aqueous sodium hydroxide solution are added, the solution is decolored with charcoal while hot and filtered. The pH of the filtrate is adjusted to 4 with concentrated hydrochloric acid. 1.6 g. of $\alpha$-(2-carboxyphenyl)-mercapto-6,7-dimethoxy-3,4-dihydro-1-isoquinolyl-acetonitrile are obtained, melting at 245° to 247° C. after recrystallization from a 1:1 mixture of DMF and water.

Analysis for $C_{20}H_{18}N_2O_4S$ (382.43): calculated: C, 62.81%; H, 4.74%; N, 7.33%. found: C, 63.03%; H, 4.85%; N, 7.05%.

EXAMPLE 17

Following the procedure described in Example 16 but starting from 1.8 g. of 1-chloromethyl-isoquinoline and 1.54 g. of thiosalicylic acid, 1.1 g. of S-(1-isoquinolyl-methyl)-2-mercapto-benzoic acid are obtained, melting at 170° to 172° C.

Analysis for $C_{17}H_{13}NO_2S$ (295.35): calculated: S, 10.86%. found: S, 10.50%.

EXAMPLE 18

To 3.2 g. of $\alpha$-carboxymethyl-mercapto-6,7-dimethoxy-3,4-dihydro-1-isoquinolyl-acetonitrile 50 ml. of absolute alcohol and 0.3 ml. of concentrated sulfuric acid are added. The reaction mixture is refluxed for six hours. The solution is evaporated to half of its volume in vacuo. Upon cooling 1.7 g. of $\alpha$-(ethoxycarbonyl)-methyl-mercapto-6,7-dimethoxy-3,4-dihydro-1-isoquinolyl-acetonitrile are obtained, melting at 128° to 130° C. after recrystallization from 96% ethanol.

Analysis for $C_{17}H_{20}N_2O_4S$ (348.42): calculated: C, 58.60%; H, 5.79%; N, 8.04%; S, 9.20%. found: C, 59.02%; H, 5.70%; N, 8.37%; S, 9.28%.

EXAMPLE 19

To 1.6 g. of α-carboxymethyl-mercapto-6,7-dimethoxy-3,4-dihydro-1-isoquinolyl-acetonitrile 5 ml. of isobutanol, 50 ml. of benzene and 3 drops of concentrated sulfuric acid are added. The mixture is refluxed for 3 hours and then is evaporated to dryness. The residue is crystallized by adding absolute ethanol. 0.7 g. of α-(2-butoxycarbonyl)-methyl-mercapto-6,7-dimethoxy-3,4-dihydro-1-isoquinolyl-acetonitrile are obtained, melting at 113° to 114° C. after recrystallization from absolute ethanol.

Analysis for $C_{19}H_{24}N_2O_4S$ calculated: C, 60.61%; H, 6.42%; N, 7.44%; S, 8.52%. found: C, 60.33%; H, 6.21%; N, 7.46%; S, 8.30%.

EXAMPLE 20

Following the procedure described in Example 19 but starting from 1.67 g. of α-(2-carboxyethyl)-mercapto-6,7-dimethoxy-3,4-dihydro-isoquinolyl-acetonitrile and 5 ml. of isobutanol 1.4 g. of α-[2-(2-butoxycarbonyl)-ethyl]-mercapto-6,7-dimethoxy-3,4-dihydro-1-isoquinolyl-acetonitrile are obtained, melting at 120° C. after recrystallization from absolute ethanol.

Analysis for $C_{20}H_{26}N_2O_4S$ (390.49): calculated: C. 61.51%; H, 6.71%; N, 7.17%; S, 8.21%. found: C, 61.14%; H, 6.70%; N, 7.35%; S, 8.48%.

EXAMPLE 21

Following the procedure described in Example 19 but starting from 1.67 g. of α-(2-carboxyethyl)-mercapto-6,7-dimethoxy-3,4-dihydro-1-isoquinolyl-acetonitrile and 5 ml. of isoamyl alcohol, 1.7 g. of α-[2-(3-methylbutoxycarbonyl)-ethyl]-mercapto-6,7-dimethoxy-3,4-dihydro-1-isoquinolyl-acetonitrile are obtained, melting at 120° C. after recrystallization from isopropanol.

Analysis for $C_{21}H_{28}N_2O_4S$ (404.52): calculated: N, 6.93%; S, 7.93%. found: N, 7.93%; S, 7.73%.

EXAMPLE 22

To 3.5 g. of α-(ethoxycarbonyl)-methyl-mercapto-6,7-dimethoxy-3,4-dihydro-1-isoquinolyl-acetonitrile 0.7 g. of hydrazine hydrate and 70 ml. of absolute ethanol are added and the reaction mixture is refluxed for 6 hours. Upon cooling 3.2 g. of α-(carbohydrazidomethyl)-mercapto-6,7-dimethoxy-3,4-dihydro-1-isoquinolyl-acetonitrile are obtained as a crystalline product melting at 192° to 194° C. after recrystallization from absolute ethanol.

Analysis for $C_{15}H_{18}N_4O_3S$ (334.39): calculated: C, 53.87%; H, 5.42%; N, 16.76%; S, 9.59%. found: C, 54.22%; H, 5.26%; N, 16.30%; S, 9.89%.

EXAMPLE 23

To 1.0 g. of α-(2-hydroxyethylmercapto)-6,7-dimethoxy-3,4-dihydro-1-isoquinolyl-acetonitrile 5 ml. of acetic anhydride and 15 ml. of benzene are added and the reaction mixture is refluxed for 4 hours. The mixture is then evaporated to dryness and to the residue carbon tetrachloride is added. 0.6 g. of α-(2-acetoxyethyl-mercapto)-6,7-dimethoxy-3,4-dihydro-1-isoquinolyl-acetonitrile are obtained, melting at 157° C. after recrystallization from butanol.

Analysis for $C_{17}H_{20}N_2O_4S$ (348.41): calculated: C, 58.60%; H, 5.79%; N, 8.04%; S, 9.20%. found: C, 58.62%; H, 5.45%; N, 8.46%; S, 8.92%.

EXAMPLE 24

To a pyridine solution of 3.2 g. of α-(carboxymethylmercapto)-6,7-dimethoxy-3,4-dihydro-1-isoquinolyl-acetonitrile 2.1 g. of dicyclohexyl-carbodiimide are added. The reaction mixture is allowed to stand at room temperature for two days. The solvent is evaporated in vacuo and the residue is recrystallized from butanol. 1.9 g. of 1-cyano-9,10-dimethoxy-3,4,6,7-tetrahydro-1,4-thiazino[3,4-a]isoquinoline-4-one are obtained, melting at 186° to 187° C. after recrystallization from butanol.

Analysis for $C_{15}H_{14}N_2O_3S$ (302.33): calculated: C, 59.59%; H, 4.66%; N, 9.27%; S, 10.61%. found: C, 59.13%; H, 4.60%; N, 8.93%; S, 10.74%.

EXAMPLE 25

To 3.2 g. of α-(carboxymethyl-mercapto)-6,7-dimethoxy-3,4-dihydro-1-isoquinolyl-acetonitrile 15 ml. of pyridine and 15 ml. of acetic anhydride are added. The solution is allowed to stand at room temperature for two days. 2.8 g. of 1-Cyano-9,10-dimethoxy-3,4,6,7-tetrahydro-1,4-thiazino[3,4-a]isoquinoline-4-one are obtained in a crystalline form. The product is identical with the product of Example 24.

EXAMPLE 26

Following the procedure described in Example 25 but starting from 3.3 g. of α-(1-carboxy-1-ethyl)-mercapto-6,7-dimethoxy-3,4-dihydro-1-isoquinolyl-acetonitrile, 2.5 g. of 1-cyano-3-methyl-9,10-dimethoxy-3,4,6,7-tetrahydro-1,4-thiazino[3,4-a]isoquinoline-4-one are obtained, melting at 170° to 171° C. after recrystallization from absolute ethanol.

Analysis for $C_{16}H_{16}N_2O_3S$ (316.38): calculated: C, 60.74%; H, 5.10%; N, 8.86%; S, 10.14%. found: C, 60.32%; H, 5.14%; N, 8.79%; S, 10.14%.

EXAMPLE 27

Following the procedure described in Example 25 but starting from 3.3 g. of α-(2-carboxyethyl)-mercapto-6,7-dimethoxy-3,4-dihydro-1-isoquinolyl-acetonitrile, 1.9 g. of 1-cyano-10,11-dimethoxy-3,4,7,8-tetrahydro-5H-1,4-thiazepino[3,4-a]isoquinoline-5-one are obtained, melting at 192° to 194° C. after recrystallization from butanol.

Analysis for $C_{16}H_{16}N_2O_3S$ calculated: C, 60.74%; H, 5.10%; N, 8.86%; S, 10.14%. found: C, 61.18%; H, 5.41%; N, 8.83%; S, 10.30%.

EXAMPLE 28

Following the procedure described in Example 24 but starting from 2.3 g. of S-(1-isoquinolyl-methyl)-thioglycolic acid, 1.1 g. of 3,4-dihydro-1,4-thiazino[3,4-a]isoquinoline-4-one are obtained, melting at 104° to 106° C. after recrystallization from absolute ethanol.

Analysis for $C_{12}H_9NOB$ (215.27): calculated: C, 66.95%; H, 4.21%; N, 6.52%; S, 14.90%. found: C, 66.64%; H, 4.44%; N, 6.48%; S, 15.06%.

EXAMPLE 29

Following the procedure described in Example 24 but starting from 2.47 g. of S-(1-isoquinolyl-methyl)-2-mercapto-propionic acid, 1.9 g. of 3-methyl-3,4-dihydro-1,4-thiazino[3,4-a]isoquinoline-4-one are obtained, melting at 67° to 68° C. after recrystallization from absolute ethanol.

Analysis for $C_{13}H_{11}NOS$ (229.30): calculated: C, 68.09%; H, 4.84%; N, 6.11%; S, 13.99%. found: C, 68.01%; H, 4.92%; N, 6.13%; S, 13.97%.

EXAMPLE 30

Following the procedure described in Example 25 but starting from 3.8 g. of α-(2-carboxyphenyl)-mercapto-6,7-dimethoxy-3,4-dihydro-1-isoquinolyl-acetonitrile, 2.7 g. of 1-cyano-12,13-dimethoxy-9,10-dihydro-7H-benzo[f]-1,4-thiazepino[3,4-a]isoqzinoline-7-one are obtained, melting at 233° to 236° C. after recrystallization from butanol.

Analysis for $C_{20}H_{16}N_2O_3$ (364.42): calculated: C, 65.91%; H, 4.43%; N, 7.69%; S, 8.80%. found: C, 65.60%; H, 4.32%; N, 7.61%; S, 8.55%.

EXAMPLE 31

Following the procedure described in Example 25 but starting from 2.95 g. of S-(1-isoquinolyl-methyl)-2-mercapto-benzoic acid, 2.1 g. of 7H-benzo[f]-1,4-thiazepino[3,4-a]isoquinoline-7-one are obtained, melting at 178° to 180° C. after recrystallization from butanol.

Analysis for $C_{17}H_{11}NOS$ (277.33): calculated: N, 5.05%; S, 11.56%. found: N, 5.00%; S, 11.82%.

EXAMPLE 32

To 1.0 g. of 1-cyano-12,13-dimethoxy-9,10-dihydro-7H-benzo[f]-1,4-thiazepino[3,4-a]isoquinoline-7-one 10 ml. of a 10% aqueous sodium hydroxide solution and 20 ml. of alcohol are added. The reaction mixture is refluxed for 8 hours, whereupon is evaporated. The residue is dissolved in water, the solution is decoloured with charcoal, filtered and acidified with a 5 N aqueous hydrochloric acid solution, 0.8 g. of α-(2-carboxyphenyl)-mercapto-6,7-dimethoxy-3,4-dihydro-1-isoquinolyl-acetonitrile are obtained, which is identical with the product of Example 16.

EXAMPLE 33

To a sodium methylate solution prepared from 0.46 g. of sodium and 50 ml. of absolute ethanol 1.1 g. of thiophenol are added. The reaction mixture is brought to the boil and a solution of 3.1 g. of α-bromo-1-cyanomethyl-6,7-dimethoxy-3,4-dihydro-isoquinoline in 100 ml. of absolute ethanol is added to the boiling solution. The mixture is boiled for another 4 to 6 hours whereupon the solvent is evaporated in vacuo. To the residue 20 ml. of absolute ethanol are added, the solution is decolored with charcoal and filtered. 2.8 g. of α-phenyl-mercapto-6,7-dimethoxy-3,4-dihydro-1-isoquinolyl-acetonitrile are obtained in a crystalline form, melting at 160° to 161° C. after recrystallization from absolute ethanol.

Analysis for $C_{19}H_{18}N_2O_2S$ (338.42): calculated: C, 67.43%; H, 5.36%; N, 8.28%; S, 9.48%. found: C, 66.83%; H, 5.49%; N, 8.39%; S, 9.39%.

EXAMPLE 34

Following the procedure described in Example 33 but starting from 3.4 g. of α-bromo-1-cyanomethyl-6,7-diethoxy-3,4-dihydro-isoquinoline and 1.1 g. of thiophenol, 2.4 g. of α-phenyl-mercapto-6,7-diethoxy-3,4-dihydro-1-isoquinolyl-acetonitrile are obtained, melting at 118° to 119° C. after recrystallization from absolute ethanol.

Analysis for $C_{21}H_{22}N_2O_2S$ (366.47): calculated: C, 68.82%; H, 6.05%; N, 7.65%; S, 8.75%. found: C, 68.81%; H, 6.51%; N, 7.34%; S, 8.62%.

EXAMPLE 35

To 5.25 g. of (α-ethoxycarbonyl)-methyl-mercapto-6,7-dimethoxy-3,4-dihydro-1-isoquinolyl-acetonitrile 20 ml. of cool absolute ethanol and 20 ml. of a cool 25% aqueous ammonia solution are added. The mixture is allowed to stand at room temperature for one day. The precipitated product is filtered off and dried to yield 3.9 g. of α-(carboxamidomethyl)-mercapto-6,7-dimethoxy-3,4-dihydro-1-isoquinolyl-acetonitrile, melting at 167° to 168° C. after recrystallization from absolute ethanol.

Analysis for $C_{15}H_{17}N_3O_3S$ (319.38): calculated: C, 56.41%; H, 5.37%; N, 13.16%; S, 10.04%. found: C, 56.59%; H, 5.49%; N, 13.21%; S, 9.91%.

EXAMPLE 36

To 1.7 g. of α-(1-carboxy-1-ethyl)-mercapto-6,7-dimethoxy-3,4-dihydro-1-isoquinolyl-acetonitrile 10 ml. of absolute ethanol and 0.2 ml. of concentrated sulfuric acid are added. The reaction mixture is refluxed for 10 hours. Upon cooling 1.6 g. of α-(1-ethoxycarbonyl-1-ethyl)-mercapto-6,7-dimethoxy-3,4-dihydro-1-isoquinolyl-acetonitrile crystallizes out from the reaction mixture. Melting point: 163° to 165° C. after recrystallization from a 75% aqueous ethanol solution.

Analysis for $C_{18}H_{22}N_2O_4S$ (362.45): calculated: C, 59.64%; H, 6.12%; N, 7.73%; S, 8.85%. found: C, 59.24%; H, 5.88%; N, 7.93%; S, 9.21%.

EXAMPLE 37

Following the procedure described in Example 33 but starting from 3.1 g. of α-bromo-1-cyanomethyl-6,7-dimethoxy-3,4-dihydroxy-isoquinoline and 1.5 g of 4-chloro-thiophenol, 3.5 g. of α-(4-chlorophenyl)-mercapto-6,7-dimethoxy-3,4-dihydro-1-isoquinolyl-acetonitrile are obtained, melting at 135° to 136° C. after recrystallization from ethyl acetate.

Analysis for $C_{19}H_{17}N_2O_2SCl$ (372.87): calculated: C, 61.20%; H, 4.60%; N, 7.51%; S, 8.60%; Cl, 9.51%. found: C, 60.99%; H, 4.65%; N, 7.60%; S, 8.70%; Cl, 9.71%.

EXAMPLE 38

Following the procedure described in Example 33 but starting from 3.1 g. of α-bromo-1-cyanomethyl-6,7-diethoxy-3,4-dihydroisoquinoline and 1.5 g. of 4-chloro-thiophenyl, 2.9 g. of α-(4-chlorophenyl)-mercapto-6,7-diethoxy-3,4-dihydro-1-isoquinolyl-acetonitrile are obtained, melting at 157° to 160° C. after recrystallization from absolute ethanol.

Analysis for $C_{21}H_{21}N_2O_2SCl$ (400.92): calculated: C, 62.91%; H, 5.28%; N, 6.99%; S, 7.90%; Cl, 8.84%. found: C, 62.43%; H, 5.26%; N, 7.10%; S, 7.56%; Cl, 8.81%.

EXAMPLE 39

8.3 g. of S-(α-cyano-α-6,7-diethoxy-3,4-dihydro-1-isoquinolyl)-methyl-isothiuronium bromide are dissolved in 80 ml. of a 96% ethanol solution and 24 ml. of a 10% aqueous sodium hydroxide solution under heating. The reaction mixture is refluxed for two hours, whereupon a solution of 4.1 ml. of ethylene-chlorohydrine in 20 ml. of absolute ethanol are added dropwise and the reaction mixture is refluxed for an additional four hours. The solvent is evaporated in vacuo and 40 ml. of water are added to the residue, 5.4 g. of α-(2-hydroxyethyl-mercapto)-6,7-diethoxy-3,4-dihydro-1-isoquinolylacetonitrile are obtained in a crystalline form, melting at 94° to 96° C. after recrystallization from ethyl acetate.

Analysis for C$_{17}$H$_{22}$N$_2$O$_3$S (334.44): calculated: C, 61.05%; H, 6.63%; N, 8.38%; S, 9.59%. found: C, 60.76%; H, 6.58%; N, 8.21%; S, 9.70%.

EXAMPLE 40

Following the procedure of Example 39 but starting from 8.3 g. of S-(α-cyano-α-6,7-diethoxy-3,4-dihydro-1-isoquinolyl)-methyl-isothiuronium bromide and 4.2 ml. of 3-chloro-propanol, 3.5 g. of α-(3-hydroxypropyl-mercapto)-6,7-diethoxy-3,4-dihydro-1-isoquinolyl-acetonitrile are obtained, melting at 100° to 105° C. after recrystallization from absolute ethanol.

Analysis for C$_{18}$H$_{24}$N$_2$O$_3$S (348.46): calculated: C, 62.04%; H, 6.94%; N, 8.04%; S, 9.20%. found: C, 61.73%; H, 6.54%; N, 8.34%; S, 8.80%.

We claim:

1. A compound of the formula (I)

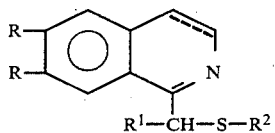

wherein
R is hydrogen, hydroxyl or C$_1$ to C$_4$ alkoxy;
R$^1$ is hydrogen, C$_1$ to C$_4$ alkyl, phenyl-C$_1$ to C$_4$ alkyl, phenyl, halo-phenyl or C$_1$ to C$_4$ alkoxy-phenyl;
R$^2$ is allyl, phenyl, halo-phenyl, C$_1$ to C$_4$ alkoxy-phenyl, carboxy-phenyl, or a group of the formula (A):

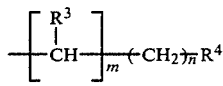

wherein
R$^3$ is hydrogen, C$_1$ to C$_4$ straight or branched chain alkyl, or phenyl;
m and n are each 0, 1 or 2 and m+n is at least 1; and
R$^4$ is hydrogen, phenyl, hydroxyl, acetoxy, carboxyl, C$_1$ to C$_6$ alkoxycarbonyl, carbamoyl, carbazoyl, or dialkylamino having 1 to 6 carbon atoms in each alkyl moiety; and
the dotted line stands for a further carbon-carbon bond or a hydrogen atoms in each of the 3- and 4-positions of the ring, or a pharmaceutically effective salt thereof.

2. α-(Ethyl-mercapto)-6,7-dimethoxy-3,4-dihydro-1-isoquinolyl-acetonitrile as defined in claim 1.

3. α-(Allyl-mercapto)-6,7-dimethoxy-3,4-dihydro-1-isoquinolyl-acetonitrile as defined in claim 1.

4. α-(2-Hydroxy-ethyl-mercapto)-6,7-dimethoxy-3,4-dihydro-1-isoquinolyl-acetonitrile as defined in claim 1.

5. α-(3-Hydroxy-propyl-mercapto)-6,7-dimethoxy-3,4-dihydro-1-isoquinolyl-acetonitrile as defined in claim 1.

6. α-(Carboxy-methyl-mercapto)-3,4-dihydro-1-isoquinolyl-acetonitrile as defined in claim 1.

7. α-(Carboxy-methyl-mercapto)-6,7-dimethoxy-3,4-dihydro-1-isoquinolyl-acetonitrile as defined in claim 1.

8. α-(2-Carboxy-ethyl-mercapto)-3,4-dihydro-1-isoquinolyl-acetonitrile as defined in claim 1.

9. α-(2-Carboxy-ethyl-mercapto)-6,7-dimethoxy-3,4-dihydro-1-isoquinolyl-acetonitrile as defined in claim 1.

10. α-(2-Carboxy-ethyl-mercapto)-6,7-diethoxy-3,4-dihydro-1-isoquinolyl-acetonitrile as defined in claim 1.

11. α-(1-Carboxy-ethyl-mercapto)-6,7-dimethoxy-3,4-dihydro-1-isoquinolyl-acetonitrile as defined in claim 1.

12. α-(2-Diethylamino-ethyl-mercapto)-6,7-dimethoxy-3,4-dihydro-1-isoquinolyl-acetonitril-hydrochloride as defined in claim 1.

13. α-(2-Dimethylamino-ethyl-mercapto)-6,7-dimethoxy-3,4-dihydro-1-isoquinolyl-acetonitril-hydrochloride as defined in claim 1.

14. α-(2-Carboxy-phenyl-mercapto)-6,7-dimethoxy-3,4-dihydro-1-isoquinolyl-acetonitrile as defined in claim 1.

15. α-(Ethoxycarbonyl-methyl-mercapto)-6,7-dimethoxy-3,4-dihydro-1-isoquinolyl-acetonitrile as defined in claim 1.

16. α-(2-Butoxycarbonyl-methyl-mercapto)-6,7-dimethoxy-3,4-dihydro-1-isoquinolyl-acetonitrile as defined in claim 1.

17. α-[2-(2-Butoxycarbonyl)-ethyl-mercapto]-6,7-dimethoxy-3,4-dihydro-1-isoquinolyl-acetonitrile as defined in claim 1.

18. α-[2-(3-Methyl-1-butoxycarbonyl)-ethyl-mercapto]-6,7-dimethoxy-3,4-dihydro-1-isoquinolyl-acetonitrile as defined in claim 1.

19. α-(Carbazoyl-methyl-mercapto)-6,7-dimethoxy-3,4-dihydro-1-isoquinolyl-acetonitrile as defined in claim 1.

20. α-(2-Acetoxy-ethyl-mercapto)-6,7-dimethoxy-3,4-dihydro-1-isoquinolyl-acetonitrile as defined in claim 1.

21. α-Phenyl-mercapto-6,7-dimethoxy-3,4-dihydro-1-isoquinolyl-acetonitrile as defined in claim 1.

22. α-Phenyl-mercapto-6,7-diethoxy-3,4-dihydro-1-isoquinolyl-acetonitrile as defined in claim 1.

23. α-(Carboxamido-methyl)-mercapto-6,7-dimethoxy-3,4-dihydro-1-isoquinolyl-acetonitrile as defined in claim 1.

24. α-(1-Ethoxycarbonyl-1-ethyl)-mercapto-6,7-dimethoxy-3,4-dihydro-1-isoquinolyl-acetonitrile as defined in claim 1.

25. α-(4-Chlorophenyl)-mercapto-6,7-dimethoxy-3,4-dihydro-1-isoquinolyl-acetonitrile as defined in claim 1.

26. α-(4-Chlorophenyl)-mercapto-6,7-diethoxy-3,4-dihydro-1-isoquinolyl-acetonitrile as defined in claim 1.

27. α-(2-Hydroxyethyl)-mercapto-6,7-diethoxy-3,4-dihydro-1-isoquinolyl-acetonitrile as defined in claim 1.

28. α-(3-Hydroxy-propyl-mercapto)-6,7-diethoxy-3,4-dihydro-1-isoquinolyl-acetonitrile as defined in claim 1.

* * * * *